(12) United States Patent
Takasawa

(10) Patent No.: US 6,993,114 B2
(45) Date of Patent: Jan. 31, 2006

(54) EXAMINATION SYSTEM, IMAGE PROCESSING APPARATUS AND METHOD, MEDIUM, AND X-RAY PHOTOGRAPHIC SYSTEM

(75) Inventor: Toru Takasawa, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 190 days.

(21) Appl. No.: 10/384,637

(22) Filed: Mar. 11, 2003

(65) Prior Publication Data

US 2004/0017894 A1     Jan. 29, 2004

Related U.S. Application Data

(60) Continuation-in-part of application No. 10/235,661, filed on Sep. 6, 2002, now abandoned, which is a division of application No. 09/407,086, filed on Sep. 28, 1999, now Pat. No. 6,501,827.

(30) Foreign Application Priority Data

Sep. 29, 1998   (JP)   .................................. 10-275231

(51) Int. Cl.
*H05G 1/64*     (2006.01)

(52) U.S. Cl. ..................................... 378/98.5; 378/116
(58) Field of Classification Search ........ 378/114–117, 378/98.5
See application file for complete search history.

(56) References Cited

U.S. PATENT DOCUMENTS

| | | | | |
|---|---|---|---|---|
| 4,200,798 | A | * | 4/1980 | Neuendorf et al. ............ 378/39 |
| 4,774,720 | A | | 9/1988 | Carbon ....................... 378/116 |
| 5,440,607 | A | | 8/1995 | Nakaya ....................... 378/116 |
| 6,078,947 | A | * | 6/2000 | Kagermeier ................ 709/203 |
| 6,501,827 | B1 | * | 12/2002 | Takasawa .................... 378/116 |
| 2002/0035572 | A1 | * | 3/2002 | Takatori et al. ........... 707/104.1 |

* cited by examiner

*Primary Examiner*—Craig E. Church
*Assistant Examiner*—Jurie Yun
(74) *Attorney, Agent, or Firm*—Fitzpatrick, Cella, Harper & Scinto

(57) ABSTRACT

A system for handling examination of an object includes an input for inputting examination request information, including a plurality of examination methods, for an object, and a performing device for performing examinations for the plurality of examination methods in an arbitrary order and obtaining results therefrom. In addition, an output outputs the results of the plurality of examination methods in a determined order regardless of an order in which the performing device has performed examinations for the plurality of examination methods.

2 Claims, 15 Drawing Sheets

FIG. 2A

| EXAMINATION ID | PATIENT INFORMATION | | | INFORMATION INDICATING RADIOGRAPHING CONTENTS | |
|---|---|---|---|---|---|
| | PATIENT ID | NAME OF PATIENT | PHYSIQUE | SEX | |
| 00000001 | 123456789 | TARO YAMADA | NORMAL | MALE | CERVICAL VERTEBRAE A→P RADIOGRAPHING REQUEST OBJECT ID 10021 RADIOGRAPHING CONDITIONS 72kV 160mA 56msec 120cm IMAGE PROCESSING PARAMETER Img.Process=D1, 3.0; C10: L5 ┈ CERVICAL VERTEBRA FORAMEN RADIOGRAPHING REQUEST OBJECT ID 10024 RADIOGRAPHING CONDITIONS 72kV 160mA 56msec 50cm IMAGE PROCESSING PARAMETER Img.Process=D1, 3.0; C10: L5 |

RADIOGRAPHING REQUEST OBJECT

FIG. 2B

| EXAMINATION ID | PATIENT INFORMATION | | | INFORMATION INDICATING RADIOGRAPHING CONTENTS |
|---|---|---|---|---|
| | PATIENT ID | NAME OF PATIENT | PHYSIQUE | SEX |
| 00000001 | 123456789 | TARO YAMADA | NORMAL | MALE | CERVICAL VERTEBRA IN FOUR DIRECTIONS RADIOGRAPHING REQUEST OBJECT ID 11000 |

RADIOGRAPHING REQUEST MENU

| RADIOGRAPHING ORDER NAME | ORDER OF REQUEST SOURCE | ORDER OF TECHNICIAN A | ORDER OF TECHNICIAN B | SERVER SHARED IN SURGERY | SERVER SHARED IN INTERNAL MEDICINE |
|---|---|---|---|---|---|
| SURGEON A THORACIC VERTEBRA IN FOUR DIRECTIONS | CERVICAL VERTEBRA FRONT → CERVICAL VERTEBRA FORAMEN → CERVICAL VERTEBRA SIDE → CERVICAL VERTEBRA RIGHT REAR OBLIQUE REGION | CERVICAL VERTEBRA FRONT → CERVICAL VERTEBRA SIDE → CERVICAL VERTEBRA RIGHT REAR OBLIQUE REGION → CERVICAL VERTEBRA FORAMEN | CERVICAL VERTEBRA FORAMEN → CERVICAL VERTEBRA FRONT → CERVICAL VERTEBRA SIDE → CERVICAL VERTEBRA RIGHT REAR OBLIQUE REGION | CERVICAL VERTEBRA FRONT → CERVICAL VERTEBRA SIDE → CERVICAL VERTEBRA FORAMEN → CERVICAL VERTEBRA RIGHT REAR OBLIQUE REGION | NOT SENT |
| SURGEON B THORACIC VERTEBRA IN FOUR DIRECTIONS | CERVICAL VERTEBRA FRONT → CERVICAL VERTEBRA FORAMEN → CERVICAL VERTEBRA RIGHT REAR OBLIQUE REGION → CERVICAL VERTEBRA SIDE | | | | |
| PHYSICIAN A THORACIC VERTEBRA IN FOUR DIRECTIONS | CERVICAL VERTEBRA FRONT → CERVICAL VERTEBRA SIDE → CERVICAL VERTEBRA ANTEFLEXION → CERVICAL VERTEBRA RETROFLEXION | CERVICAL VERTEBRA FRONT → CERVICAL VERTEBRA ANTEFLEXION → CERVICAL VERTEBRA RETROFLEXION → CERVICAL VERTEBRA SIDE | CERVICAL VERTEBRA SIDE → CERVICAL VERTEBRA FRONT → CERVICAL VERTEBRA ANTEFLEXION → CERVICAL VERTEBRA RETROFLEXION | NOT SENT | CERVICAL VERTEBRA FRONT → CERVICAL VERTEBRA SIDE → CERVICAL VERTEBRA ANTEFLEXION → CERVICAL VERTEBRA RETROFLEXION |
| PHYSICIAN B THORACIC VERTEBRA IN FOUR DIRECTIONS | ... | | | | |

FIG. 10

EXAMINATION SYSTEM, IMAGE PROCESSING APPARATUS AND METHOD, MEDIUM, AND X-RAY PHOTOGRAPHIC SYSTEM

CROSS-REFERENCE TO RELATED APPLICATION

This application is a continuation-in-part of application Ser. No. 10/235,660, filed Sep. 6, 2002 now abn., which is a divisional of application Ser. No. 09/407,086, filed Sep. 28, 1999 U.S. Pat. No. 6,501,827.

BACKGROUND OF THE INVENTION

1. Field of the Invention

The present invention relates to an examination system suitable for an X-ray photographic system, for example, for taking an order from a doctor for the taking of an X-ray photograph (radiograph) and for performing X-ray photography (radiography), to an image processing apparatus and method, and to a medium therefor.

2. Description of the Related Art

An "X-ray photographic apparatus" refers to an apparatus for detecting X-rays, which have been transmitted through a patient, to form an image. This image is formed by representing differences in the transmittance of each type of the tissue structure in the body of the patient and the thickness thereof as a photography density. It is important for a good X-ray image that as much information as possible be displayed in a readily visible manner. The position of the patient, the direction of X-ray irradiation, photographic conditions, etc., exert large influences thereon. Accordingly, when a doctor orders an X-ray photograph be taken, X-ray information such as the area to be X-rayed, the X-raying directions, the X-raying methods, etc., is typically specified together with patient information such as the name and the ID number of the patient. The information is then sent to a technician, and the X-raying is performed. If a plurality of X-ray photographs are to be taken, X-ray photographic request information, together with the patient information such as the name and the ID number of the patient, is included in the X-ray photograph order, for example, "chest portion A→P," "chest portion R→L," "cervical vertebra R→L," or "cervical vertebra A→P."

FIG. 12 shows an X-ray photographic system in which an X-ray photographic apparatus and an X-ray generation apparatus are combined, which shows an example contrasted to the present invention. In FIG. 12, reference numeral 100 denotes an X-ray tube for emitting X-rays. Reference numeral 101 denotes an X-ray generation apparatus. Reference numeral 102 denotes an operation and display section of the X-ray generation apparatus, for performing operation of the X-ray generation apparatus. These are usually collectively termed an "X-ray generation apparatus". On the other hand, the X-ray photographic apparatus comprises a standing position sensor unit 103 capable of performing X-ray photography of a patient in a standing position, a recumbent position sensor 105, an X-ray photographic system control section 107 for controlling this sensor, and an operation and display section 108 of the X-ray photographic system. Also, reference numeral 104 denotes a standing position sensor panel, and reference numeral 106 denotes a recumbent position sensor panel. The electrical charge corresponding to the amount of transmitted X-rays, detected by the standing position sensor panel 104 and the recumbent position sensor panel 106, is converted for analog into digital form and is input as an electronic image to the X-ray photographic system control section 107. Also, reference numeral 110 denotes a network which is connected to an imager 111.

When patient reception has been completed, a patient proceeds to a section of a corresponding examination department (for example, brain surgery, internal medicine, surgery, orthopedic surgery, etc.), and the patient's illness is diagnosed. For example, there are cases in which, in order to examine cervical vertebrae in a surgery department, it is desirable to see X-ray images of cervical vertebrae taken from four different directions. Examples of the four directions of the cervical vertebrae include "cervical vertebrae, front," "cervical vertebrae, foramen," "cervical vertebrae, side," and "cervical vertebrae, right rear oblique region."

The "cervical vertebrae, front" is obtained by a method in which the X-ray photograph is taken when the patient is made to stand facing the X-ray generation apparatus. Adjustments are made so that the forehead is horizontal to the standing position sensor panel 104, and the angle and position of the X-ray tube 100 are adjusted so that X-rays can be emitted toward the fourth cervical vertebra of the patient. In a method for properly positioning the "cervical vertebrae, foramen," the patient is made to lie supine on the recumbent position sensor unit 105, the mouth is opened to the fullest, the line connecting the head in the median plane to the external ear foramen and the line connecting the base of the nose to the external ear foramen are made perpendicular to each other, and the X-ray tube is set to be perpendicular to the recumbent position sensor panel 106 so that the radiation focus is at the head in the median plane. In a method for properly positioning the "cervical vertebrae, side," the patient is made to stand facing 90 degrees away from the standing position sensor unit 103, the jaw is made to project forward slightly, the shoulders are made to lower, and the X-ray focus becomes incident on the fourth cervical vertebra. In a method for properly positioning the "cervical vertebra, right rear oblique region," the standing position sensor panel 104 and the patient form an angle of 50°, with the shoulder being the center; then, the jaw is made to project forward slightly, and the shoulders are made to lower.

A doctor writes the order for the X-ray photographing of the cervical vertebra in four directions on a radiology record card. At this time, the photographing order is written in the order in which the doctor wishes to subsequently view the images. For example, the order may be "cervical vertebra, front"→"cervical vertebra, foramen"→"cervical vertebra, side"→"cervical vertebra, right rear oblique region." Alternatively, there are cases in which the photographing order is indicated by "cervical vertebra, four directions." At this time, the meanings indicated by "cervical vertebra, four directions" may differ depending on the examination department (i.e., in the brain surgery department, "cervical vertebra, front"→"cervical vertebra, side"→"cervical vertebra, anteflexion"→"cervical vertebra, retroflexion"), the sequence may differ from doctor to doctor, and the sequence may differ depending upon the facilities.

The patient, with this radiology record card in hand, proceeds to the radiotherapy department and submits it to the receptionist. When it is the patient's turn to be X-rayed, the patient is taken to a room in which the X-ray photographic system in FIG. 12 is disposed. The technician first examines the patient information such as the ID number and the name written on the radiology record card, confirms the identity of the patient and then inputs this data by using the operation and display section 108. This data is required to confirm a match between the images and the patient and to assist the doctor in interpreting the images. Next, after the technician reads the X-ray photography order written on the radiology record card, the patient is correctly positioned; at the operation console 102 of the X-ray generation apparatus, the tube voltage, the tube current, and the irradiation time or the photo-timer are set; and in the operation console 108 of the X-ray photographic apparatus, image processing parameters, the imager 111 of the transfer destination, etc., are set to perform X-ray photography.

First, a case is described in which X-ray photography is conducted in the order as written on the radiology record card. The technician, after reviewing the radiology record card, performs X-ray photography of the "cervical vertebra, front." The patient is made to stand facing the X-ray generation apparatus, and adjustments are made so that the forehead is parallel to the standing position sensor panel 104. Also, the angle and position of the X-ray tube 100 are adjusted so that X-rays can be emitted toward the fourth cervical vertebra of the patient. At this time, the position of the X-ray tube 100 is such that X-rays are emitted toward the fourth cervical vertebra of the patient from 15° below the fourth cervical vertebra. Examples of the X-ray photographic conditions are as follows: the distance between the standing position sensor panel 104 and the X-ray tube 100 is 120 cm, the tube voltage of the X-ray tube 100 is 72 kV, the tube current is 160 mA, the irradiation time is 56 msec, and the cross grid and the tube are focused on a small area. After the photographic preparations are completed and photography is possible, the irradiation switch in the vicinity of the operation and the display section 102 of the X-ray generation apparatus is pressed, and X-rays are emitted from the X-ray tube 100 to the standing position sensor unit 103. X-rays emitted from the X-ray tube 100 pass through the patient and are converted into electricity of various amounts by the standing position sensor panel 104. This electricity is then amplified by an amplifier, signal processing, such as analog/digital conversion, is performed thereon, and the result is obtained as a digital image. The image input to the control section 107 of the X-ray photographic system is subjected to various image processings, such as gradation processing or highlight processing, and is displayed on the operation and display section 108 of the X-ray photographic system. The technician examines the image, and if it is necessary to retake the X-ray photograph, a rephotographing key is then pressed to retake the image. If it is not necessary to retake the X-ray photograph, then the technician performs second and subsequent X-ray photography in a similar manner.

X-ray photography is then performed for "cervical vertebra, foramen," "cervical vertebra, side," and "cervical vertebra, right rear oblique region." When the photography of the "cervical vertebra, four directions" is completed, the termination key is pressed to transfer the four obtained images to the imager 111 via the network 110 so that the images are displayed on film, and these images are passed on to the doctor for examination. However, since the X-ray photography of the "cervical vertebra, foramen" for the second photography is performed by the photographic apparatus with the patient in a recumbent position, the proper positioning of the patient is time-consuming, causing problems in that this is burdensome and the rate at which X-rays may be taken is low.

Next, a case is described in which the X-ray photographic technician performs X-ray photography in a sequence in which it is easier to take the X-rays, regardless of the sequence in which the doctor has requested them. It is common practice for the technician to take the X-rays with as little effort as possible and in a sequence in which the burden on the patient is minimized. Since the recumbent position sensor unit 105 is used for only the "cervical vertebra, foramen," and at this time the patient must be moved a great deal and the position of the X-ray tube must be substantially changed, it is efficient for X-ray photography other than the "cervical vertebra, foramen" to be performed continuously to reduce the burden on the patient. For example, X-ray photography is performed in the sequence "cervical vertebra, front"→"cervical vertebra, right rear oblique region"→ "cervical vertebra, side"→"cervical vertebra, foramen." In this case, after X-ray photography of the "cervical vertebra, four directions" is terminated, the photographs are transferred via the network 110 in the sequence in which they were taken by the imager 111. Consequently, they must be transferred to film and must be rearranged in the sequence in which the doctor wishes to examine them to perform diagnosis.

In recent years, there have been cases in which networks are constructed with the intra-hospital information systems called "HIS" and radiology information systems called "RIS," and requested data from the diagnosis department and patient information from the HIS server are transmitted via the network and are input. Even in this case, the above-described problems remain.

In a manner as described above in the first X-ray photography situation, there is a problem in that proper positioning cannot be performed efficiently when the predetermined photographic sequence is inconvenient for the technician; therefore, the photographing efficiency is decreased, and the burden on the patient is substantial. In the second X-ray photography situation, effort is subsequently required to rearrange the sequence of the image films into that which the doctor wishes to see, and this is also inconvenient. Another problem is that there is no effective means to confirm the order of the part currently being X-rayed and to confirm which part is photographed last. In addition, a problem arises in that when an X-ray must be retaken, this retake must be performed before the next part is X-rayed.

As described above, there are problems in that when X-ray photography is to be performed in a requested sequence, the photographing efficiency may be decreased, and in that the rearrangement of the sequence to that in which the doctor will view the images after the X-ray photographs are taken is very complicated. In addition, problems occur in that it cannot be confirmed which part in the photographing order is currently being photographed, and in that when the image is blurred, retake cannot be performed quickly. Such problems occur not only in the above-described examination apparatus, but also in other photography, for example, in a case in which images from a consumer digital camera are printed out.

SUMMARY OF THE INVENTION

An object of the present invention is to overcome the above-described problems.

Another object of the present invention is to provide an apparatus capable of taking X-ray photographs using a plurality of photographic methods with easy operation, which are easy to understand for both the requestor (for example, a doctor) and the operator (for example, a technician).

Another object of the present invention is to provide an apparatus capable of taking a large number of X-ray photographs, in which it is easy to determine the photographs which are yet to be taken in the photographing order, the portion currently being photographed, and the portions which have already been photographed.

Another object of the present invention is to provide an image processing method and apparatus having new features, a medium, and an X-ray photographic system.

To achieve the above-mentioned objects, according to a first aspect of the present invention, there is provided an examination system comprising: an input device for inputting the sequence of a plurality of examination methods for a patient; a changing device for changing the input sequence; a performing device for performing the examination in accordance with the changed sequence; and an output device for outputting in a desired sequence a plurality of examination results performed by the performing device.

According to a second aspect of the present invention, there is provided an image processing apparatus comprising: an instruction device for instructing a plurality of photographs be taken with respect to an object image in a predetermined sequence; a changing device for changing the sequence by the instruction device; and an output device for outputting in the predetermined sequence a plurality of images photographed in accordance with a sequence changed by the changing device.

According to a third aspect of the present invention, there is provided an image processing method, comprising the steps of: instructing a plurality of photographs be taken with respect to an object image in a predetermined sequence; receiving a changing of sequence by the instruction device and changing the sequence; and outputting in the predetermined sequence a plurality of images photographed in accordance with a sequence changed by the changing device.

According to a fourth aspect of the present invention, there is provided a computer-executable storage medium for storing a program, the program comprising the steps of: instructing a plurality of photographs be taken with respect to an object image in a predetermined sequence; receiving a changing of sequence by the instruction device and changing the sequence; and outputting in the predetermined sequence a plurality of images photographed in accordance with a sequence changed by the changing device.

According to a fifth aspect of the present invention, there is provided a photographic system for irradiating a patient with X-rays and for digitally obtaining an X-ray transmitted image, the photographic system comprising: an X-ray photographic apparatus for performing X-ray photography in given examination units; an apparatus for inputting, to the X-ray photographic apparatus, patient data and photographic request information from which setting parameters required for the X-ray photographic apparatus to perform a photography can be created; an operation device for displaying the system status and for performing an operation; an input device for inputting photographic request information formed of a plurality of photographic requests with respect to one patient data; a creation device for creating setting parameters required to perform photography from the plurality of input photographic requests; and a device for calling and setting the created setting parameters.

According to a sixth aspect of the present invention, a system for handling examination of an object includes input means for inputting examination request information, including a plurality of examination methods, for an object; and performing means for performing examinations for the plurality of examination methods in an arbitrary order and obtaining results therefrom. In addition, output means outputs the results of the plurality of examination methods in a determined order regardless of an order in which the performing means has performed examinations for the plurality of examination methods.

According to a seventh aspect of the present invention, a system for handling examination of an object includes input means for inputting request information, including a plurality of examination methods arranged in an order, for an object; changing means for changing the order into a changed order; and performing means for performing examinations in accordance with the changed order and obtaining results therefrom. Output means outputs the results of the plurality of examination methods in a determined order regardless of the changed order.

According to an eight aspect of the present invention, a method adapted to a system for handling examination of an object comprises the steps of inputting examination request information, including a plurality of examination methods, for an object; and performing examinations for the plurality of examination methods in an arbitrary order and obtaining results therefrom. The results of the plurality of examination methods are output in a determined order regardless of an order in which examinations for the plurality of examination methods have been preformed in said performing step.

According to a ninth aspect of the present invention, a method adapted to a system for handling examination of an object includes the steps of inputting examination request information, including a plurality of examination methods arranged in an order, for an object; changing the order into a changed order; and performing examinations in accordance with the changed order and obtaining results therefrom. The results of the plurality of examination methods are output in a determined order regardless of the changed order.

With such a construction, it is possible to efficiently take X-ray photographs in a sequence desired by the photographer (technician) regardless of the sequence in the requested photographic order.

The above and further objects, aspects and novel features of the invention will become more apparent from the following detailed description when read in connection with the accompanying drawings.

BRIEF DESCRIPTION OF THE DRAWINGS

FIGS. 2A and 2B show the content of photographic request information.

FIG. 10 shows a photographing order conversion table.

DESCRIPTION OF THE PREFERRED EMBODIMENTS

First Embodiment

Figure 1:
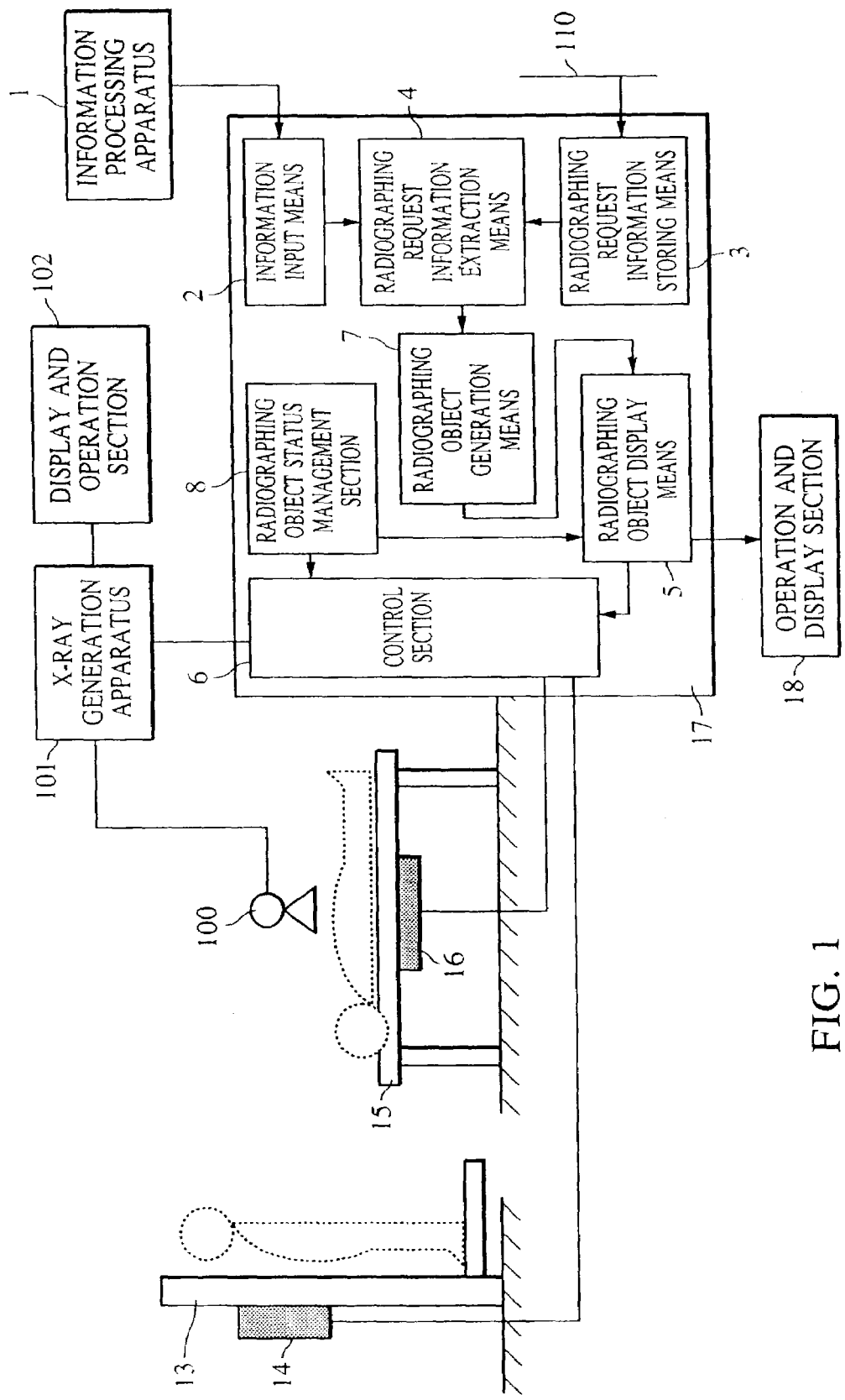
FIG. 1 is a configuration view of an X-ray photographic system according to a first embodiment of the present invention.

FIG. 1 shows the system configuration of an X-ray photographic system according to a first embodiment of the present invention.

Figure 12:
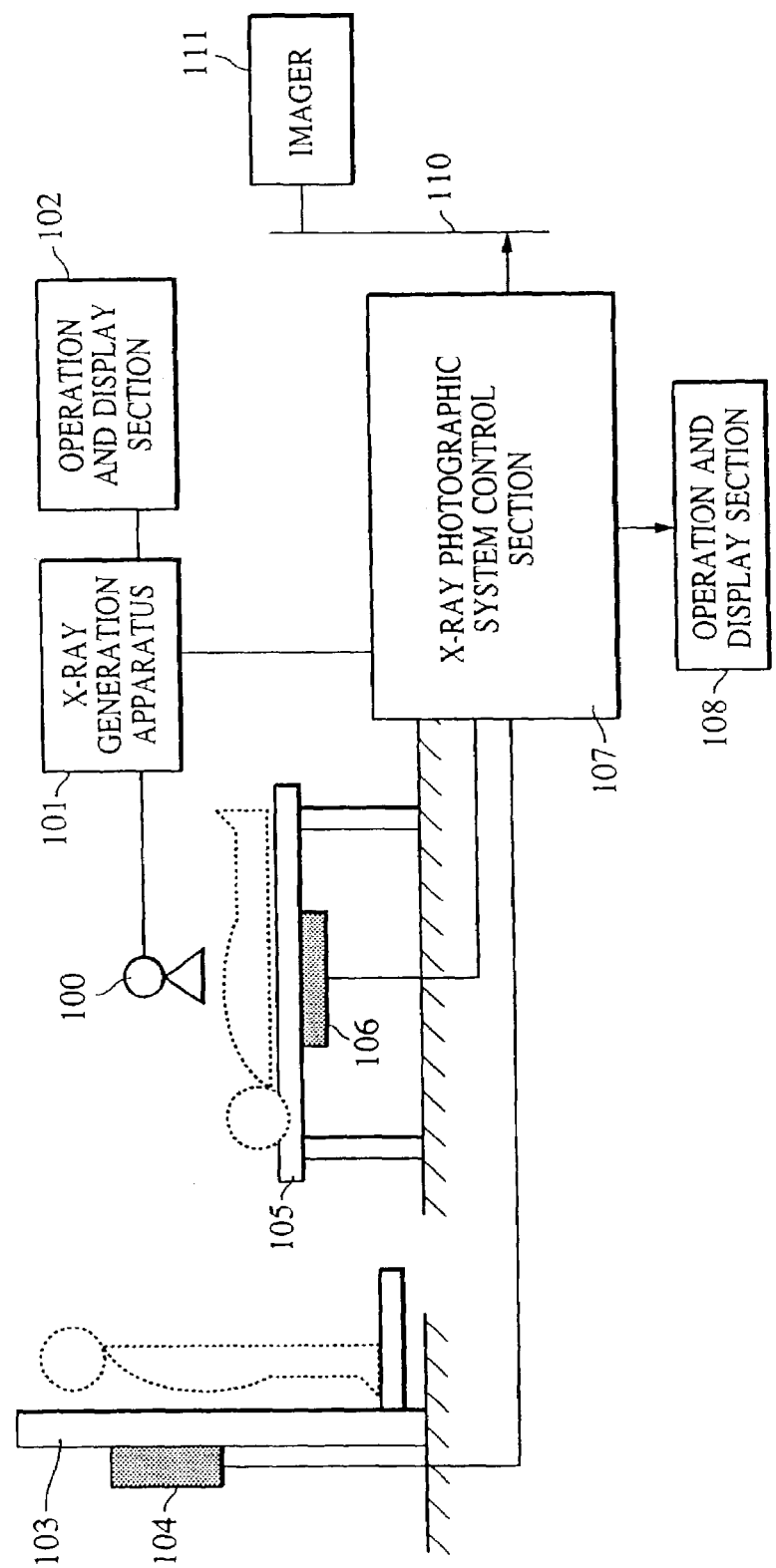
FIG. 12 shows an X-ray photographic system, which is a comparative example of the present invention.

Components in FIG. 1 which are the same as those of FIG. 12 described earlier designate the same. This X-ray photographic system (radiography system) comprises a standing position sensor unit 13, a recumbent position sensor unit 15, an X-ray generation apparatus 101, an operation and display section 102 of the X-ray generation apparatus, a control section 17 of an X-ray photographic (radiography) apparatus, an operation and display 18 of the X-ray photographic apparatus, and an information processing apparatus 1.

In FIG. 1, reference numeral 1 denotes an information processing apparatus for reading the contents of magnetic stripes of a magnetic card, and reference numeral 2 denotes information input means for inputting an examination ID read by the information processing apparatus 1. Reference numeral 3 denotes photographic request information storing means for inputting and memorizing photographic request information input via a network 110. A trigger by which the photographic request information is input may be from the X-ray photographic apparatus control section 17 or may be from a server of the network 110. Reference numeral 4 denotes photographic request information extraction means which functions to extract desired photographic request information from the photographic request information stored in the photographic request information storing means 3 on the basis of the examination ID information input by the information input means 2. The examination ID is an identification number of the photographic request information. The extracted photographic request information is formed of one patient information, and one or more photographic request objects indicating the photographic contents or a photographic request menu. The photographic request menu is formed of a plurality of photographic request objects, for example, items of the photographic request menu include a photographing of cervical vertebra in four directions discussed in the comparative example. The photographic request object represents a photographing unit, and is often classified by the photographic region name or by the photographic region name and the photographic method. This photographic request object has a unique photographic request name or a photographic request object ID as an identification number for the purpose of identification. The photographic conditions and the image processing parameters may be or may not be entered. When the photographic conditions and the image processing parameters are entered, a search is performed in the previous photography, and the photographic conditions and the image processing parameters at that time are set. If it is a first photography, the standard photographic conditions which are the default values for each photographic request object ID are entered. When the photographic conditions and the image processing parameters are not entered, these items are created based on the photographic request object ID through a photographic object creation means 7 in the X-ray photographic system.

Reference number 7 denotes a photographic object creation means for conversion from a photographic request object ID into a photographic object ID. A unique symbol, in addition to the photographic conditions, such as the tube voltage, the tube current, the irradiation time, and image processing conditions, is provided in the obtained photographic object ID, and a photographic object having the symbol displayed thereon is created on the operation and display section 18 of the X-ray photographic apparatus. The symbol may of course be graphics rather than text. Reference number 8 denotes a photographic object status management section for managing the status of each of the photographic objects. Reference numeral 5 denotes a photographic object display means for producing a display corresponding to the status from the photographic object status management section 8. Reference number 6 denotes a control section for sending and setting the photographic conditions, such as the tube voltage, the tube current, and the irradiation time, of the selected photographic object ID to the X-ray generation apparatus 101 and the sensor panels 13 and 15, and for sending the image processing parameters to the control section 6 in order to specify image processing.

FIGS. 3, 4, 5, 6, and 7 are detailed views of an operation and display section 18 of an X-ray photographic system of FIG. 1. Reference numeral 111 denotes a touch panel formed of a liquid-crystal display and an analog-resistance-film-type touch sensor sheet. Reference numeral 112 denotes a mouse. Reference numeral 113 denotes cables, such as a power supply and a control line. The display is performed by the touch panel 111, and the operation can be performed from either the touch panel 111 or the mouse 112. The cables 113 comprise a power supply, a VGA cable, a serial cable for controlling the touch panel, and a serial cable for a mouse. Reference numeral 114 denotes a photographic image display area for displaying the photographic image. Reference numeral 115 denotes a patient information display area for displaying the patient information. Reference numeral 116 denotes a photographic object parameter display area for displaying the parameter of the photographic object. Reference numeral 117 denotes a photographic object display area for displaying photographic objects of one patient in a list according to the status. Reference numeral 118 denotes a message area for displaying the status of the system and a message. Reference numeral 119 denotes a change switch which is used when the photographic conditions and the image processing parameters are changed.

Figure 9:
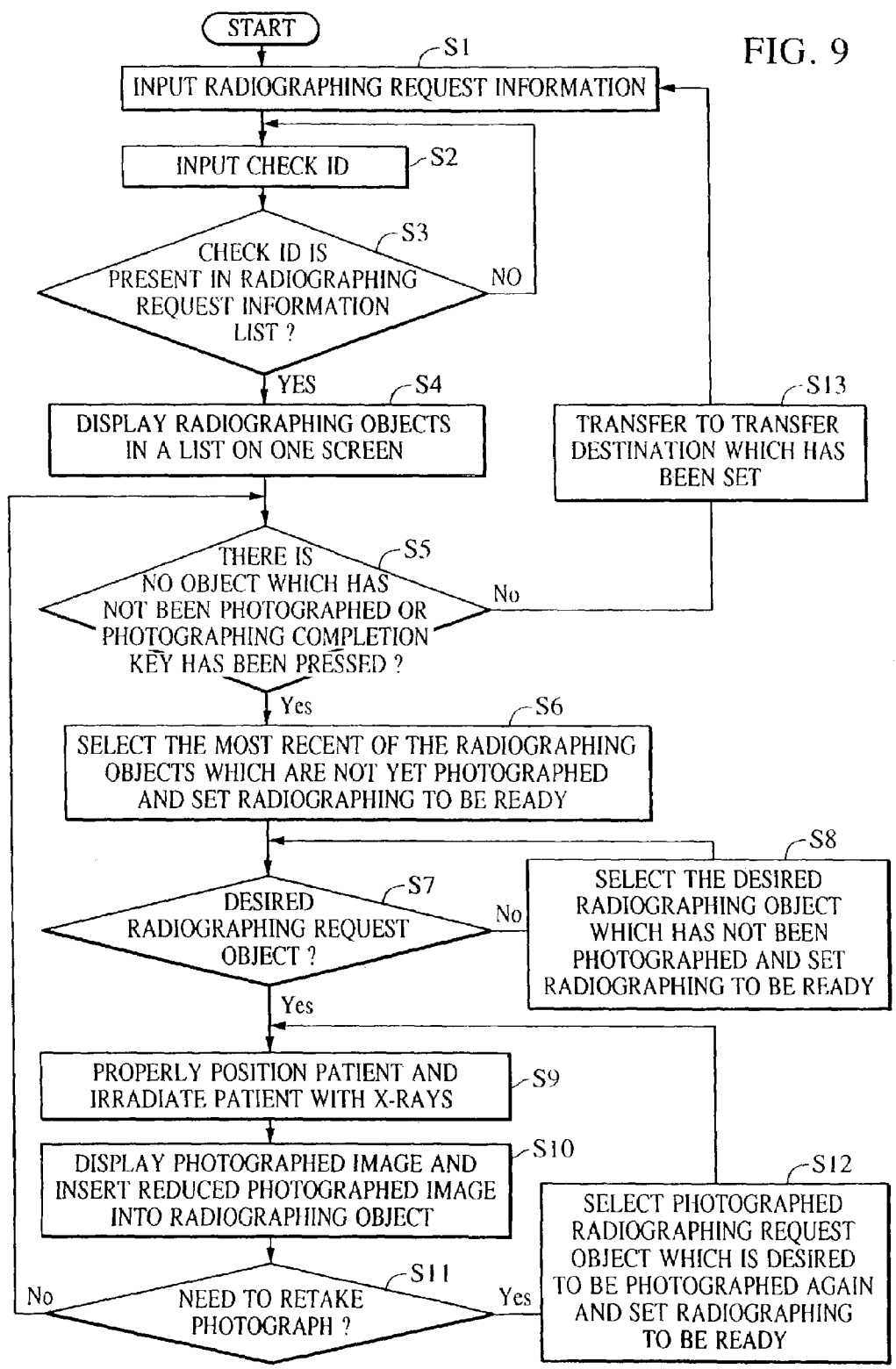
FIG. 9 is a flowchart according to the first embodiment of the present invention.

FIG. 9 is a flowchart according to the first embodiment of the present invention.

Referring to FIGS. 3, 4, 5, 6, and 7 above, the first embodiment of the present invention is described below. A case is described in which cervical vertebrae in four directions are to be photographed, which was described in the comparative example.

An X-ray image is formed by representing differences in the transmittance of the type of the tissue structure in the body of the patient and the thickness thereof as a photographic density. It is important for a good X-ray image that as much information as possible be displayed in a readily visible manner. The position of the patient, the direction of X-ray irradiation, photographic conditions, etc., exert large influences thereon. The photographic posture of the patient differs according to the region for the object of photography, the photographic direction, and the irradiation method, and further, according to the body type of the patient. For example, in the "cervical vertebra, front" photography, the patient is made to stand facing the X-ray generation apparatus, the head is slightly raised so that the forehead is horizontal to the sensor panel, the ends of the cutting teeth of the middle upper jaw are adjusted so that the plane including the right and left nipple-shaped projections becomes horizontal, and further, the angle and position of the X-ray tube 100 is adjusted so that X-rays can be emitted to the fourth cervical vertebra of the patient from 15° below the fourth cervical vertebra. If the photographic posture is unnatural, the alignment of the body of vertebra cannot be faithfully represented or the region which should be taken note of is hidden, thereby obstructing a diagnosis. The combination of this photographing posture and the irradiation angle is sometimes called a "photographing method".

Examples of the photographing conditions include the setting of the X-ray generation apparatus, such as the tube voltage, the tube current, and the irradiation time; the setting of the irradiation area and the threshold value of the photo-timer; the size of an image to be obtained; and the grid movement speed. In the case of a photographic apparatus capable of digitally obtaining an X-ray image, image processing to be performed on the obtained image exerts a large influence. Examples of the image processing include a white correction process, a sensor output correction process such as a gain correction process, a gradation process, changing of type of a density conversion curve, changing of density and contrast, DR compression, and QA processing such as highlight processing. The above-described photographic conditions and the image processing are often determined by the photographic regions, the photographic methods, and the physique of the patient. Accordingly, the photographic request issued from the doctor includes the photographic regions, the photographic methods, and the physique of the patient.

When patient reception has been completed, the patient proceeds to the surgery department and submits a patient's case record and a magnetic card, in which the ID number of the patient is recorded, to the receptionist of the surgery department. The doctor calls the personal data of the patient inside the server of the network of the intra-hospital information system called "HIS" by using the patient ID number of the magnetic card as the search key at the terminal. The doctor performs a medical examination while using this personal data as a reference. When photography of cervical vertebra in four directions is to be performed as a result of the medical examination, the doctor issues the photographic request information from the terminal to the radiation section. For example, it is assumed that the photographic request information is formed of four photographic request objects: the patient name 'Taro Kanon" as the patient information, the ID number "123456789", the physique "normal", and the photographing order "cervical vertebra AP," "cervical vertebra, foramen," "cervical vertebra LR," and "cervical vertebra, right rear oblique region." At this time, the examination ID "0000001" is issued. This is a number different from patient to patient, and is recorded on the magnetic card possessed by the patient. The doctor, after issuing the order, passes this magnetic card to the patient and instructs the patient to proceed to the radiation section.

This photographic request information issued from the terminal of the surgery department is transferred to the X-ray photographic system of the photographic room shown in FIG. 1 via the intra-hospital information system HIS and the radiology information system RIS. This photographic request information is stored in the photographic request information storing means 3 of FIG. 1. On the other hand, when the patient arrives at the photographic room, the technician loads the magnetic card into the information processing apparatus 1 in order to read the examination ID number. The read examination ID number is immediately input via the information input means 2. Then, in the photographic request information extraction means 4, the photographic request information of the patient is extracted by finding a matching examination ID number from the stored photographic request information. The photographic object creation means 7 creates a corresponding photographic object by referring to the photographic request object ID, the photographic request name, the physique of the patient, etc., contained in the extracted photographic request information. At this time, when the photographic conditions and the image processing parameters are not contained in the photographic request object, default values for each photographic object are set. In a case in which photography of any one of the recumbent position and the standing position is possible as in the "cervical vertebra, foramen," the default value for the type of the sensor is also present. The photographic objects are displayed in a photographic method object display section 117 shown in FIGS. 2A and 2B in the sequence in which the doctor has instructed by the photographic object display means 5. At this time, the status management section 8 sets the first photographic object to the "selected state" and sets the status of the photographic objects other than that to the "photographic wait state". For example, the "selected state" is displayed in a state in which the key is pressed, and the "photographic wait state" is displayed in a state in which the key is not pressed. The parameters called by the photographic object ID are the photographic conditions, the image processing parameters, the photographing range, and the set value of the photo-timer. The photographic conditions are: the tube voltage of 72 kV, the tube current of 160 mA, the irradiation time of 56 msec, and the focal length of 120 cm. The image processing parameters are: Img.Process=D1, 3.0;C10;L5 (as the parameters of Img.Process, for example, the first area is at a density 3.0, the contrast γ=10, and a fifth function is used as the density conversion table). The photographic range is a 2688×2688 pixel area, and only the center of the photo-timer is enabled. If these settings are performed individually, a lot of time and labor is taken, and therefore, all are performed by pressing the photographic object. The parameters are transferred to the X-ray generation apparatus 101 shown in FIG. 1 so that the tube voltage, the tube current, and the irradiation time are set, and the photographic range and the set values of the photo-timer, etc., are sent to the standing position sensor unit 13 used for photography. Also, the image processing parameters are set at this point in time.

Figure 3:
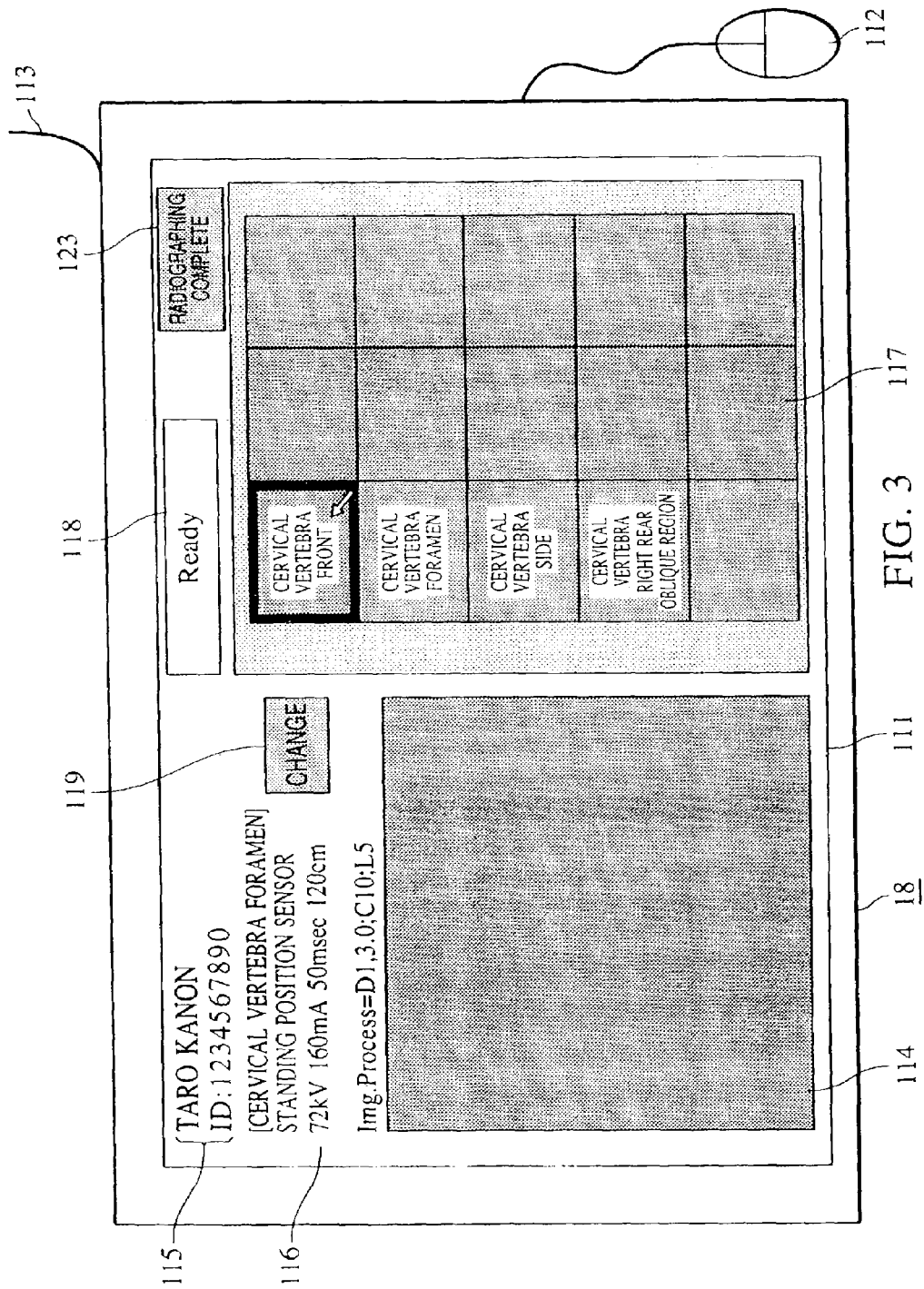
FIG. 3 shows the displayed contents of an operation and display section of the X-ray photographic system at the time a first photograph is taken, according to the first embodiment of the present invention.
Figure 4:
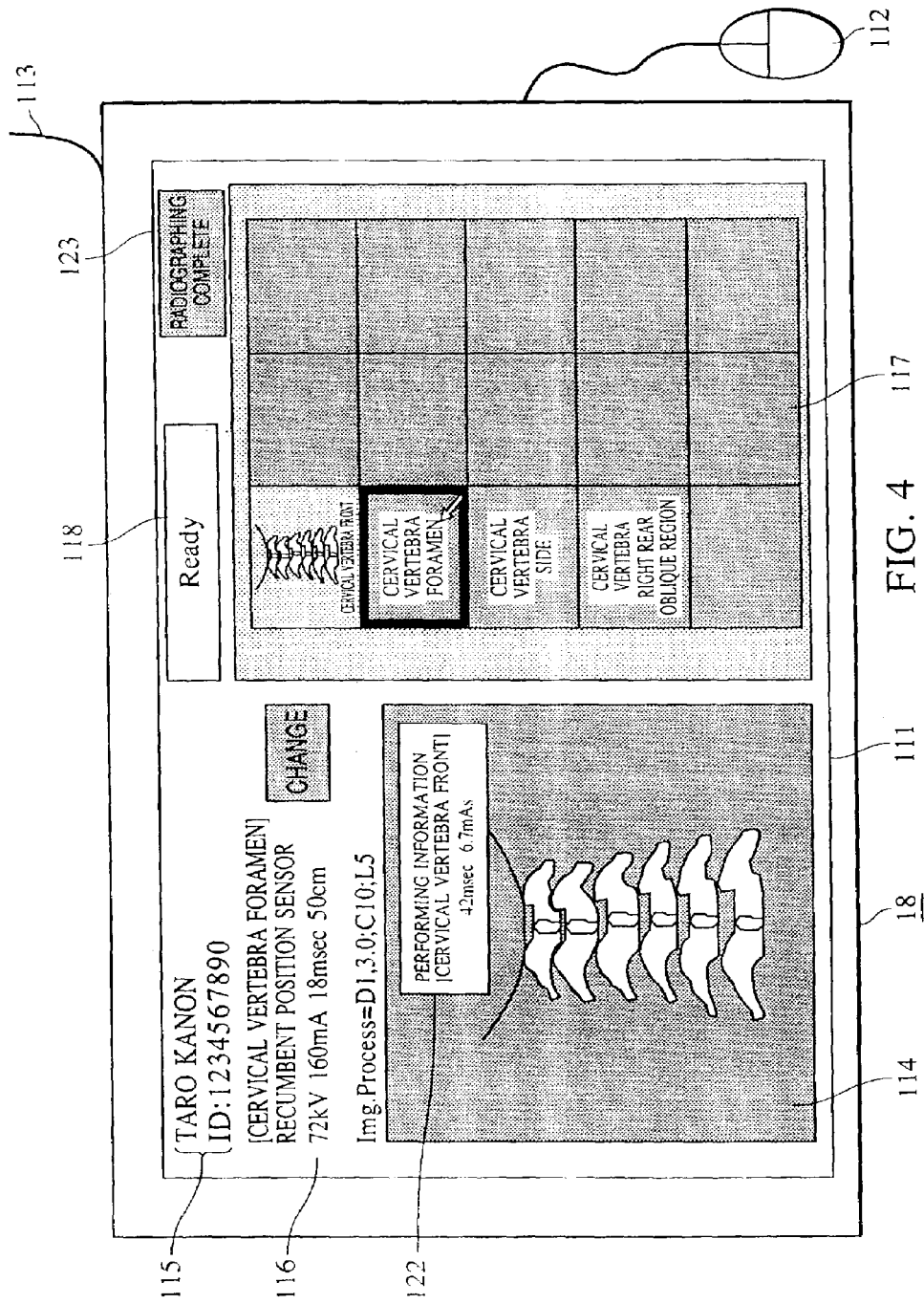
FIG. 4 shows the displayed contents of the operation and display section of the X-ray photographic system after the first photograph has been taken, according to the first embodiment of the present invention.
Figure 5:
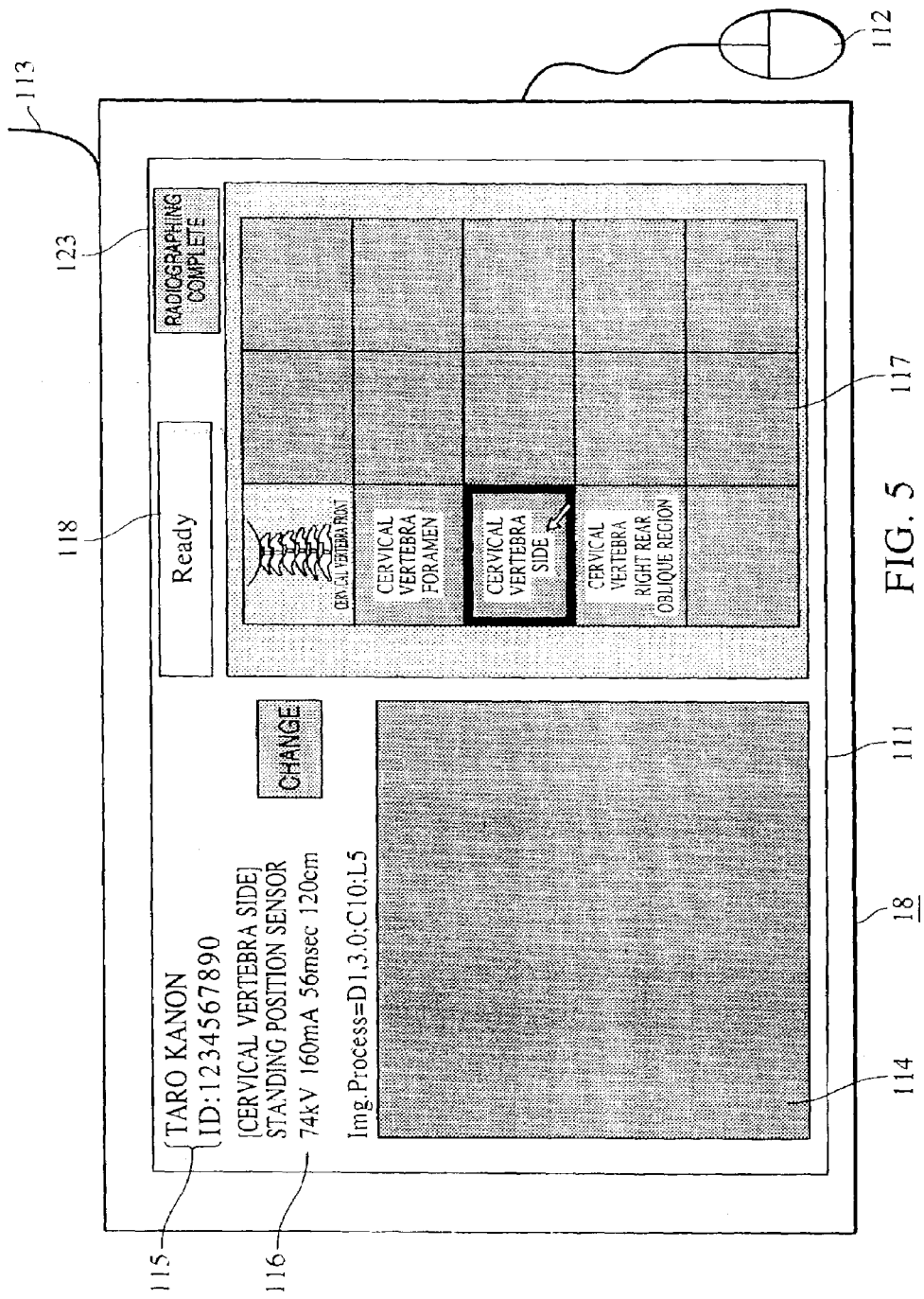
FIG. 5 shows the displayed contents when a second photographic method in the operation and display section of the X-ray photographic system is changed according to the first embodiment of the present invention.
Figure 6:
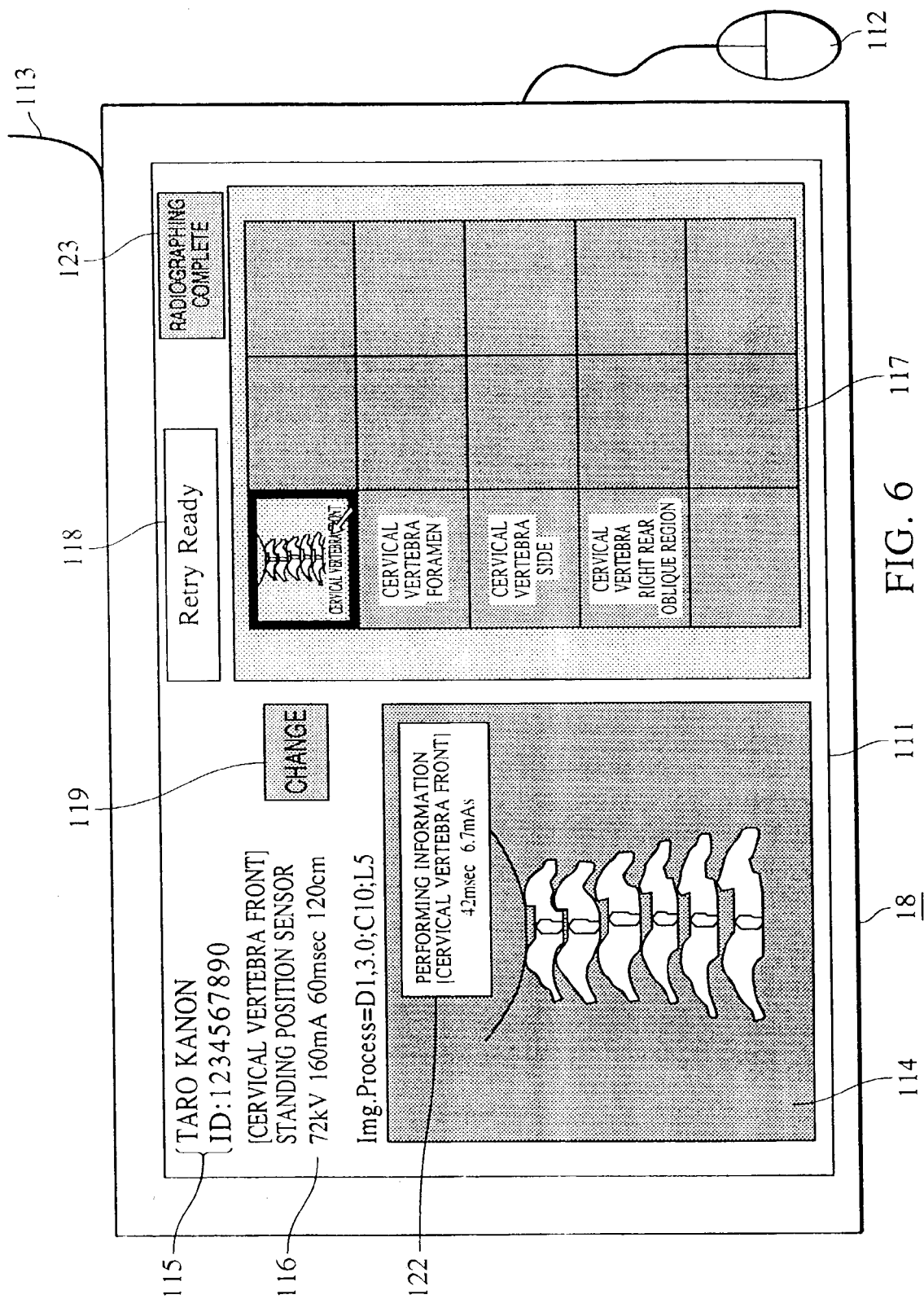
FIG. 6 shows the displayed contents when the first image in the operation and display section of the X-ray photographic system is to be retaken according to the first embodiment of the present invention.
Figure 7:
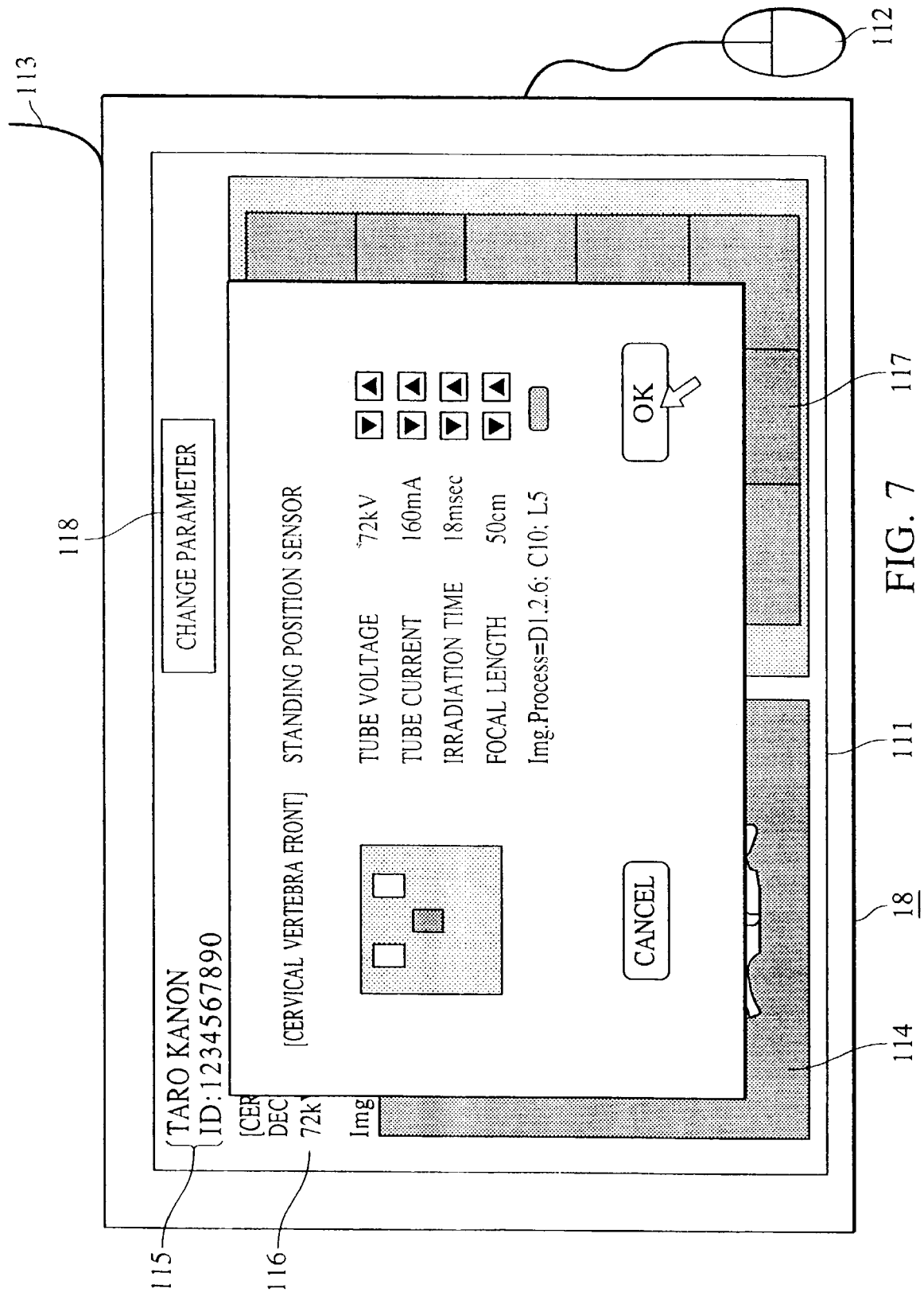
FIG. 7 shows the displayed contents of a change dialogue for a photographic method parameter of the operation and display section of the X-ray photographic system according to the first embodiment of the present invention.

The display at this time is as shown in FIG. 3. The name and the ID number of the patient are displayed in the patient information display area 115; the photographic conditions and the image processing conditions are displayed in the photographic object parameter display area 116; and a state in which the "cervical vertebra, front" is selected is displayed in the photographic object display section 117. If these conditions are OK, the patient is properly positioned, and photography is performed by irradiating X-rays. When, however, a change is required, the change switch 119 is pressed to call a parameter change dialogue such as that shown in FIG. 7 in order to change various parameters. When all are completed, X-rays are irradiated to obtain an X-ray image. The photographed image as shown in FIG. 4 is displayed in the photographic image display area 114, and the photographic object status management section 8 changes the status of the "cervical vertebra, front" of the photographic object to "photographed". Also, since the photographic method object of the "cervical vertebra, front" is changed to "photographed," the photographic object display means 5 displays a reduced image of the "thoracic vertebra, front," instead of displaying the "cervical vertabra, front," and displays performing information, such as the irradiation time and the mAs value, on a performing information window 122 (see FIG. 5). This performing information is also added to the photographic object. Then, the next "cervical vertebra, foramen" is set to the "selected state" on the basis of the information the doctor has requested so that a photographic ready state is reached. Here, if the "cervical vertebra, side" is desired to be photographed earlier, the "cervical vertebra, side" switch of the photographic object display section 117 is pressed. As shown in FIG. 5, the parameters of the photographic object of the "cervical vertebra, side" are then transferred to the X-ray generation apparatus 101 of FIG. 1 as described earlier, so that the tube voltage, the tube current, and the irradiation time are set, the photographing range and the set values of the photo-timer, etc. are sent to the standing position sensor unit 103 used for photography. The image processing parameters are also set at this point in time, and the system changes to a photographic ready state. Furthermore, when a photograph is to be retaken, the "cervical vertebra, front" key in which the reduced image of FIG. 3 is displayed is pressed. Then, since the status of the photographic object of the "cervical vertebra, front" is determined to be "photographed" by the photographic object status management section 8 of FIG. 1, the photographed image of the "cervical vertebra, front" is displayed in the photographic image display area 114, the parameters of the photographic object are displayed in the photographic object parameter display area 116, and the system is made to transition to the re-photographing ready state in the "cervical vertebra, front." FIG. 6 shows the display state at that time. When all the photography has been completed in the above procedure, a photographic completion key 123 is pressed so that the process proceeds to a photographic completion process. The photographed images are rearranged in the requested sequence ("cervical vertebra, front"→"cervical vertebra, foramen"→"cervical vertebra, side'→"cervical vertebra, right rear oblique region") and are output to the image server of RIS and the imager. The patient information, the information of the changed photographic object, etc., together with the image information, are also transferred to the image server. The transfer destination is set in advance on a system setting screen (not shown).

The above sequence is described with reference to the flowchart of FIG. 9. In steps S1 and S2, photographic request information is input from the intra-hospital information system HIS, the radiology information system RIS, etc., and an examination ID is input from input means. When it is determined in step S3 that there is photographic request information corresponding to the examination ID input in step S2, the photographic objects are displayed in a list in the requested order (step S4). If the photographing key has not been pressed or if there is an object which is not yet photographed, the first photographic object of the objects which are not yet photographed is made selectable (step S6). After a confirmation is made as to whether it is a desired photographic object (step S7), the patient is properly positioned, and a photograph is taken by irradiating X-rays (step S9). After the photograph is taken, the photographed image is displayed, and the reduced image thereof is embedded in the photographic object and is displayed (step S10). When there is no need to re-take (step S11), the process proceeds to the next photographic step (step S5 and subsequent steps). When a re-take is to be performed, the photographed photographic object in which re-taking is desired is selected, and the photographic ready state is set to take a photograph (steps S12, S9, and S10). When there is no photographic object which has not been photographed or when the photographic completion key is pressed (step S5), the photographs are transferred to the transfer destination in the requested sequence (step S13), and photography of the next examination ID is performed.

In a manner as described above, when a plurality of photographs are requested, the display of the photographic object is replaced with the photographed image after the photograph is taken. Consequently, there are advantages in that it can be quickly determined for which of the photographing plans the current photographic method is positioned, re-photographing can be performed at a timing desired by the technician, and it is difficult to make a mistake because the image to be re-taken is displayed. In addition, there is the advantage in that since photographs are transferred to the image server and the imager in the sequence requested by the doctor even if the photographs are taken in any sequence, it is easy for the doctor to diagnose. Here, although a magnetic card is used to find the examination ID, similar advantage can be obtained even if other information recording media, such as bar codes or IC cards, are used.

In the X-ray photographic system described in the first embodiment, a magnetic card is used to find the examination ID, and the photographs are displayed in the photographic method object display section 117 by the photographic object display means 5 in the sequence instructed by the doctor. However, facilities exist in which no magnetic card is used. The reason for this is that there is a risk in that a magnetic card might be lost or magnetic stripes might be damaged. In that case, the oldest photographic request information in the examination order list is selected, the first photographic object of the photographic request is selected, and the system is made to transition to a photographic ready state. If the examination ID is to be changed, the examination list is displayed, and a desired examination ID is selected from the list.

Second Embodiment

The sequence of the photographic request objects is fixed by a doctor and a technician and by implementation after being put into practical use in particular medical facilities. Therefore, it is effective that a correspondence table is created in advance and the photographic order is converted in accordance with the table. This table is referred to when photographic request information is extracted by the photographic request information extraction means 4 in FIG. 1 and when photographs are transferred to the image server and the imager after the photographs are taken. Then, the sequence of the photographic request objects is automatically converted on the basis of the request information and the status of a technician switch 120 and a transfer destination switch 121.

Figure 8:
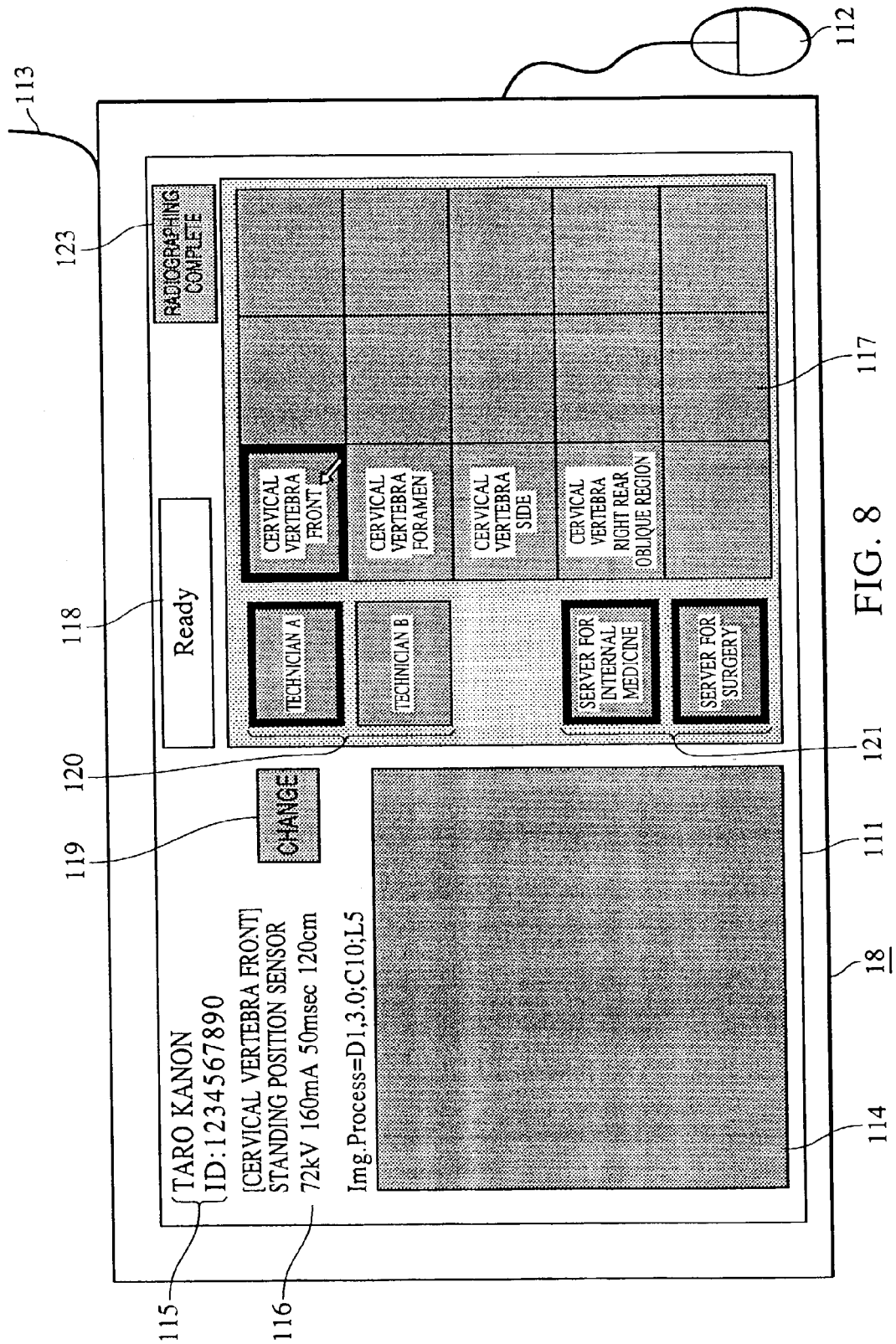
FIG. 8 shows the displayed contents of an operation and display section of an X-ray photographic system according to a second embodiment of the present invention.

FIG. 10 shows an example of this conversion table. In this case, the operation and display section 18 is as shown in FIG. 8. Reference numeral 120 denotes a technician switch, which is a key for identifying a technician who controls the X-ray photographic system. Reference numeral 121 denotes a transfer destination switch, which is a switch for selecting a transfer destination. The default of the transfer destination switch is determined by the photographic request information. Assuming that a technician A is selected as the technician switch 120, when photographic request information of a surgeon A for thoracic vertebra in four directions is received, a display is produced in the sequence of "cervical vertebra, front"→"cervical vertebra, side"→"cervical vertebra, right rear oblique region"→"cervical vertebra, foramen" as in the photographic method object display section 117 of FIG. 8. Also, after the photographs are taken, they are transferred to the requester in the requested sequence and are transferred to the server shared for surgery in the sequence such as "cervical vertebra, front"→"cervical vertebra, side"→"cervical vertebra, foramen"→"cervical vertebra, right rear oblique region".

Figure 11:
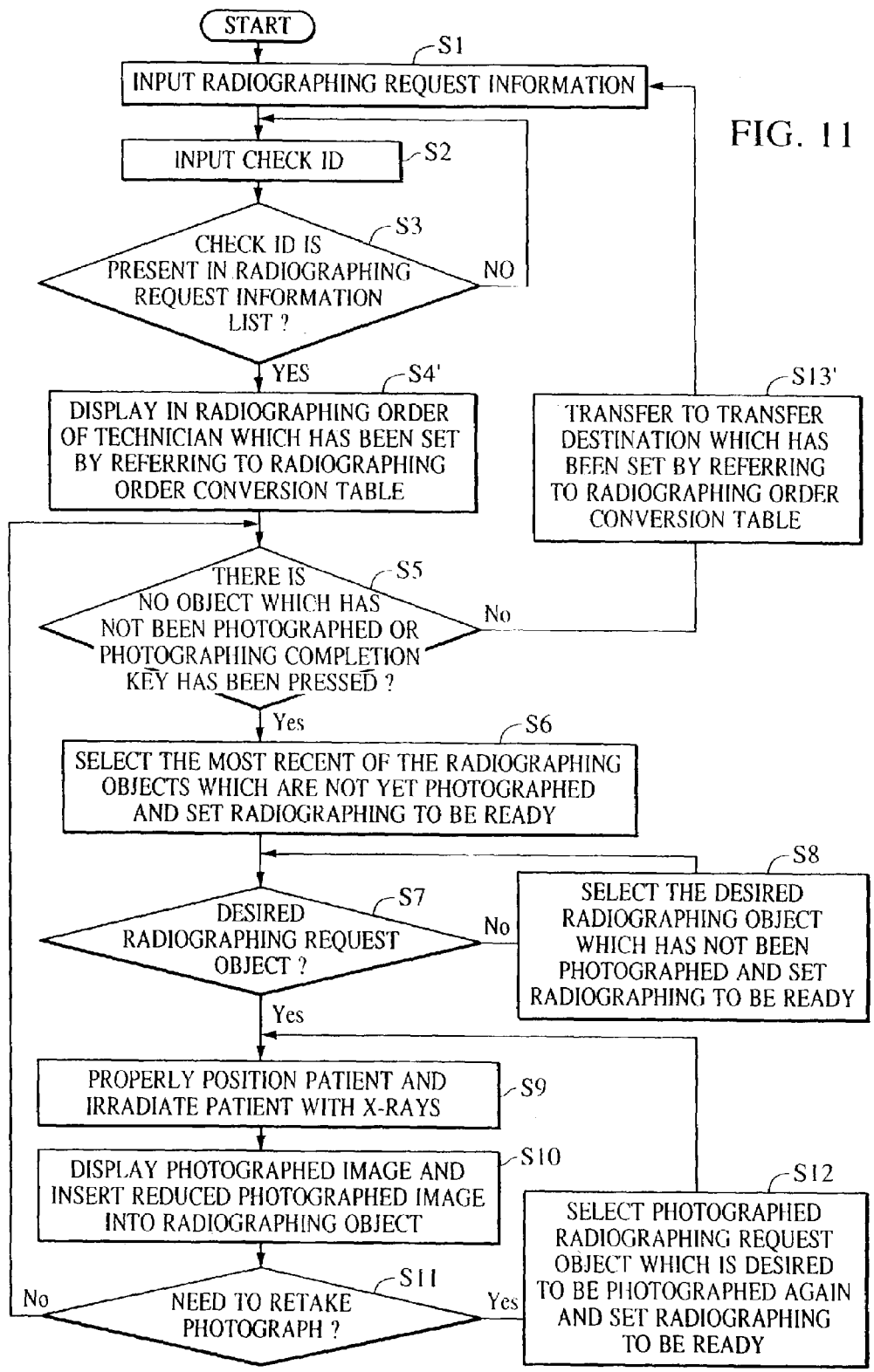
FIG. 11 is a flowchart according to the second embodiment of the present invention.

FIG. 11 is a flowchart according to a second embodiment of the present invention. Steps S4' and S13' are different from those of the first embodiment. By referring to the photographic order conversion table in both steps, the photographic sequence is rearranged in a predetermined sequence desired by the doctor, and transferring is performed in a predetermined sequence.

In a manner as described above, the sequence can be automatically changed and transferred for each transfer destination, thereby yielding the advantage that the operation is easy.

In the above-described embodiments, a system comprising an X-ray photographic apparatus is disclosed. In addition, without being limited to such a system, the present invention can be applied to, for example, a system comprising a consumer digital camera and printer.

An apparatus which changes a prespecified photographic sequence in order to take a photograph and which prints out in a specified sequence different from the sequence in which photography is performed actually is included in the present invention.

Another Embodiment of the Present Invention

The present invention may be applied to a system comprising a plurality of apparatuses (for example, a host computer, an interface apparatus, a reader, a printer, etc.) or to a single apparatus (for example, a copying machine, a facsimile apparatus, etc.).

Also, an embodiment is included within the scope of the present invention, in which program codes of software for realizing the above-described embodiments are supplied to a computer within an apparatus or a system connected to various devices so that the various devices are operated to realize the functions of the above-described embodiments, and the computer (CPU or MPU) of the system or the apparatus causes the various devices to operate in accordance with the stored program.

In this case, the program codes of the software themselves realize the functions of the above-described embodiments, and the program codes themselves and a means, for example, a storage medium storing such program codes, for supplying the program codes to a computer, comprises the present invention.

As storage media for storing such program codes, for example, floppy disks, hard disks, optical disks, magneto-optical disks, CD-ROMs, magnetic tape, non-volatile memory cards, ROMs, etc., may be used.

Not only in a case in which the functions of the above-described embodiments are realized by executing supplied program codes by a computer, but also in a case in which the functions of the above-described embodiments are realized by the program codes in collaboration with an OS (operating system) running in a computer or in collaboration with other application software, it is a matter of course that such program codes are included in an embodiment of the present invention.

In addition, it is a matter of course that a case is also included in the present invention, in which after supplied program codes are stored in a memory provided in a function expansion unit connected to a function expansion board of a computer or connected to a computer or a CPU which is provided in a function expansion board or in a function storage unit, performs a part or the entirety of actual processing in accordance with the instructions of the program codes, and the functions of the above-described embodiments are realized by the processing.

It is to be understood that the present invention may also be applied to a system including a plurality of apparatuses (e.g., radiation generating apparatuses, radiographic apparatuses, image processing apparatuses, interface apparatuses, and image output apparatuses, etc.) and to a single apparatus in which functions of these apparatuses are integrated. When the present invention is applied to a system including a plurality of apparatuses, the apparatuses are connected with one another via, for example, an electric connecting device (communication device), an optical connecting device (communication device), and/or a mechanical connecting device, and/or the like.

Figure 13:
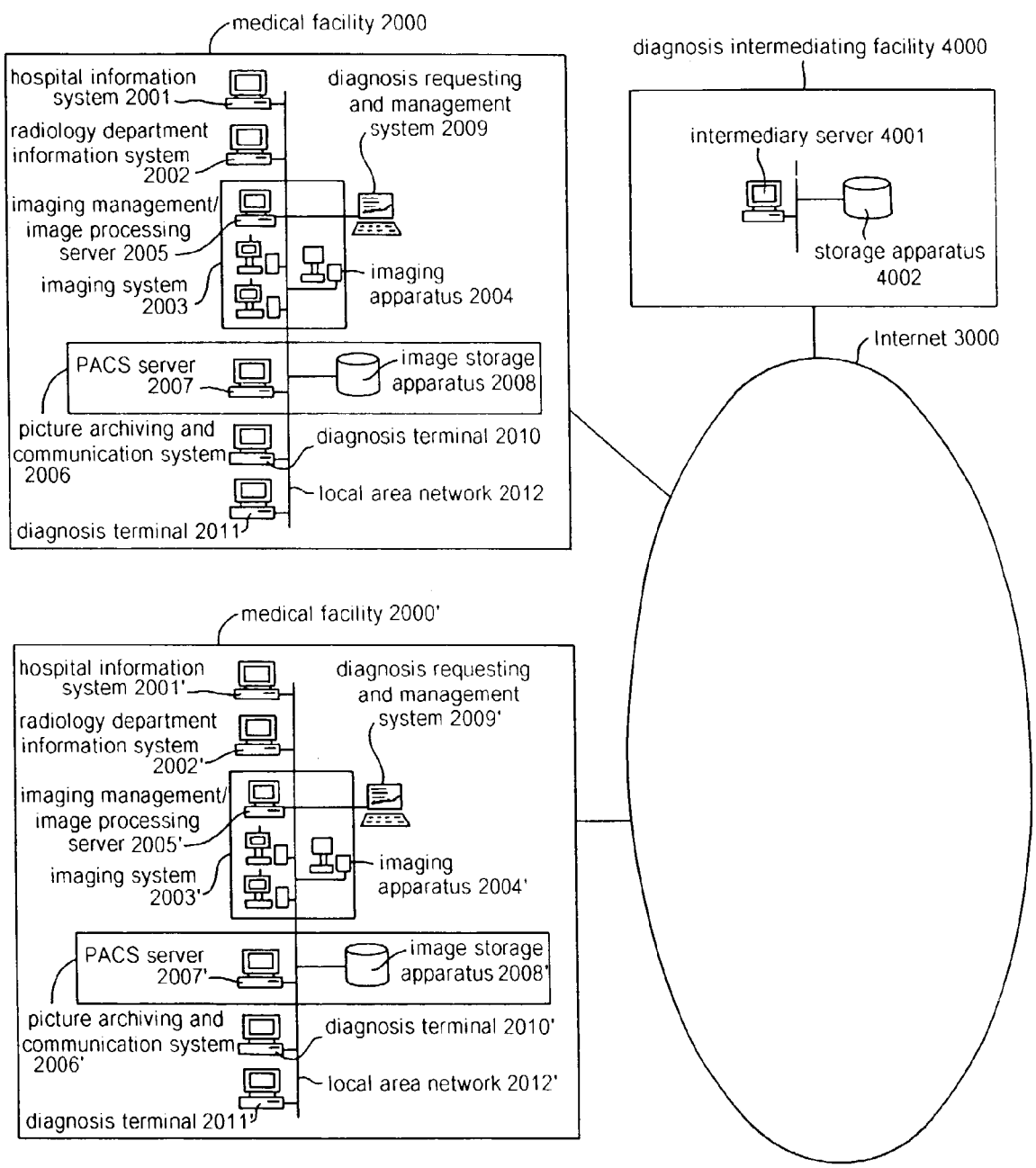
FIG. 13 shows an image diagnosis aiding system including a network.

Furthermore, the present invention may also be applied to an image diagnosis aiding system including a network (LAN and/or WAN, etc.) shown in FIG. 13. Referring to FIG. 13, information regarding a patient that has come to a medical facility 2000 (e.g., carte information, examination information, according information, etc.) is managed by a hospital information system (hereinafter abbreviated as HIS) 2001 including a computer or computer network, etc. A radiology department information system (hereinafter referred to as RIS) 2002 including a computer or computer network, etc. manages information in a radiology department, and for example, it manages a radiography request information from the HIS in cooperation with an imaging system (radiographic system) 2003 to be described later.

The imaging system 2003 is used for radiography, and it includes, for example, at least one imaging apparatus 2004 for radiographing a patient and outputting image data, and an imaging management/image processing server 2005 for management of radiographing based on radiography request information from the RIS, etc., and/or image processing of radiographs, etc. The imaging system 2003 or the imaging apparatus 2004 includes, for example, the system shown in FIG. 1 described above.

A picture archiving and communication system (hereinafter abbreviated as PACS) 2006 includes, as a function, archiving image data from the imaging system 2003 together with information required for management of the image data and/or image diagnosis, etc. (also referred to as attached information) and providing the image data (and the attached information) as needed. The PACS 2006 includes, for example, a PACS server 2007 including a computer or computer network, and an image storage apparatus 2008 for storing the image data and the attached information.

A diagnosis requesting and management system 2009 operates in cooperation with the imaging system 2003 and/or the PACS 2006, etc., transmitting diagnosis request information for image data acquired by the imaging system 2003 to a diagnostician automatically or based on an operation by an operator (e.g., radiological technologist) so as to serve the image data to image diagnosis (image interpretation by the diagnostician), and executing management of progress of image diagnosis, etc. The diagnosis requesting and management system 2009 includes a computer or computer network, etc.

Diagnosis terminals (image viewers, etc.) 2010 and 2011 are used by diagnosticians, and each of the diagnosis terminals 2010 and 2011 includes a computer or computer network, etc. that is capable of, for example, receiving diagnosis request information from the diagnosis requesting and management system 2009, retrieving image data and attached information from the PACS 2006, inputting diagnostic result by a diagnostician, transmitting information indicating the result of diagnosis and/or completion of diagnosis to the diagnosis requesting and management system 2009, etc.

The above components 2001 to 2011 are connected with one another via a LAN (local area network) 2012. The diagnostic result information is transmitted from the diagnosis requesting and management system 2009 or directly from the diagnosis terminals 2010 and 2011 to at least one of the hospital information system 2001, the radiology department information system 2002, and the PACS 2006.

Destination of the diagnosis request from the diagnosis requesting and management system 2009 is not limited to that within the medical facility 2000. For example, diagnosis may be requested to a diagnostician of another medical facility via a WAN (wide area network) utilizing a public line or a private line. FIG. 13 shows an example where the medical facility 2000 is connected to another medical facility 2000' via the Internet 3000. The medical facility 2000' herein includes, without limitation, components 2001' to 2012' similarly to the medical facility 2000. The diagnosis requesting and management system 2009 of the medical facility 2000 is capable of requesting diagnosis to, for example, the medical facility 2000' via the Internet 3000 and the diagnosis requesting and management system 2009' of the medical facility 2000', and obtaining result of diagnosis therefrom.

Furthermore, instead of the system in which diagnosis request information, image data, and diagnosis result information are directly exchanged among medical facilities, a system including a diagnosis intermediating facility 4000 may be implemented. In that case, for example, the diagnosis requesting and management system 2009 of the medical facility 2000 transmits diagnosis request information including image data to the diagnosis intermediating facility 4000 via the Internet 3000. The diagnosis intermediating facility 4000 is owned by a diagnosis intermediating service agency (diagnosis intermediating service company, etc.), and it includes an intermediary server 4001 including a computer or computer network, and a storage apparatus 4002 that stores data as needed.

The intermediary server 4001 have the functions of selecting a medical facility and/or a diagnostician that is suitable for diagnosis based on the diagnosis request information from the medical facility 2000, transmitting the diagnosis request information to the selected medical facility and/or diagnostician, providing image data, etc., as needed to the medical facility and/or the diagnostician, obtaining diagnosis result information from the medical facility and/or the diagnostician, providing the diagnosis result information and other relevant information to the medical facility 2000, and so forth. The storage apparatus 4002 stores, in addition to the diagnosis request information, data required for executing the above functions, such as data required for selecting a medical facility and/or a diagnostician suitable for diagnosis (e.g., data concerning network address, field of diagnostic ability, diagnostic skill, schedule, etc of the medical facility and/or the diagnostician). According to the system configuration, the diagnosis requesting and management system 2009 of the medical facility 2000 is allowed to receive diagnosis result information from a medical facility and/or a diagnostician that is suitable for diagnosis via the Internet 3000 and the diagnosis intermediating facility 4000.

The medical facility 2000 is not limited to hospitals, and may be, for example, a medical examination and diagnosis agency where a diagnostician works, in which case the medical facility 2000 is replaced by a medical examination and diagnosis agency 2000" (not shown) including components similar to the components 2003 to 2012. Furthermore, the medical facility 2000 may be a medical examination agency where only medical examination (e.g., radiography) is performed. In that case, for example, medical facility 2000 is replaced by a medical examination agency 2000''' (not shown) including components similar to the components 2003 to 2009 and 2012.

Furthermore, part of the systems, apparatuses, units, or the functions in the medical facility 2000 (e.g., the image processing unit 12 or part of the functions thereof in the imaging system 2003 or the imaging apparatus 2004) may reside outside the medical facility 2000, and may be replaced, for example, by similar systems, apparatuses, units, or functions in other facilities via the Internet 3000.

Figure 14:
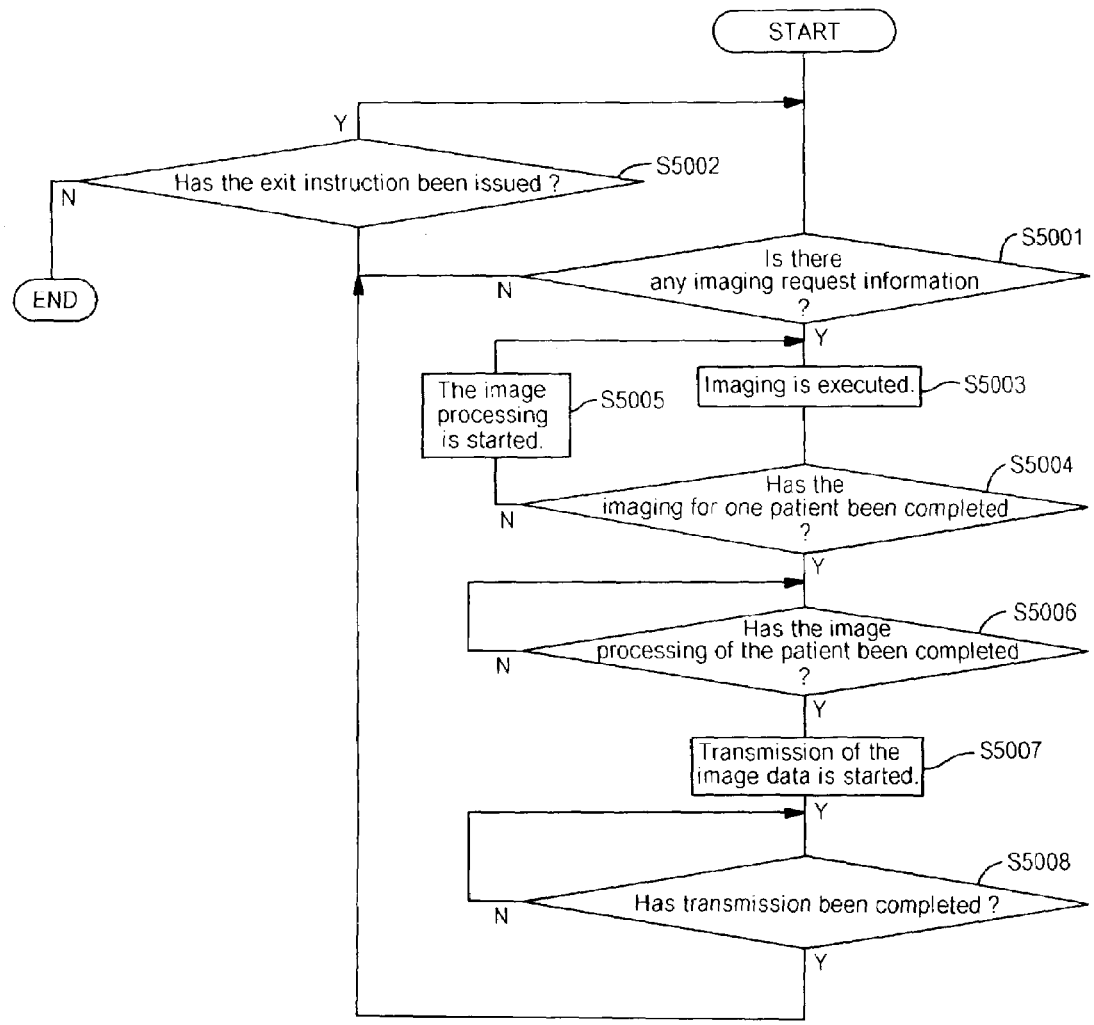
FIG. 14 is a flowchart of an imaging system according to the present invention.

Now, a procedure of processing by the imaging system 2003 and the diagnosis requesting and management system 2009 in the medical facility 2000 will be described. First, a procedure of processing executed by the imaging system 2003 will be described with reference to a flowchart shown in FIG. 14. First, in step S5001, the imaging system 2003 determines whether any imaging request information has been transmitted from the HIS or RIS. If any imaging request information is found, the imaging system 2003 proceeds to step S5003, whereas it proceeds to step S5002 if no imaging request information is found. In step S5002, the imaging system 2003 determines whether an exit instruction has been issued thereto. If an exit instruction has been issued, the imaging system 2003 exits processing. If no exit instruction has been issued, the imaging system 2003 returns to step S5001 to continue processing. In step S5003, the imaging system 2003 executes imaging as in the embodiments described earlier.

After execution of imaging, the imaging system 2003 determines whether all the imaging requested for one patient is completed (step S5004). If imaging is not completed, the imaging system 2003 starts image processing of a radiograph acquired by previous imaging in step S5005, and returns to step S5003 to continue imaging process. At this time, the image processing is executed as in the embodiments described earlier, and in parallel with the imaging process in step S5003. When imaging is completed for the patient, the imaging system 2003 proceeds to step S5006.

In step S5006, the imaging system 2003 determines whether image processing of all the images of the patient, acquired by imaging is completed. If image processing for all the images is completed, the imaging system 2003 proceeds to step S5007. If the image processing is not completed, the determination in step S5006 is repeated.

In step S5007, the imaging system 2003 starts transmission of all the image data, of the patient, that has been processed. For example, all the image data is transmitted to the PACS 2006, and data for accessing the image data transmitted to the PACS 2006 is transmitted to the diagnosis requesting and management system 2009.

In step S5008, the imaging system 2003 determines whether transmission of the image data is completed. If the transmission is completed, the imaging system 2003 proceeds to step S5002. If the transmission is not completed, the determination in step S5008 is repeated.

Figure 15:
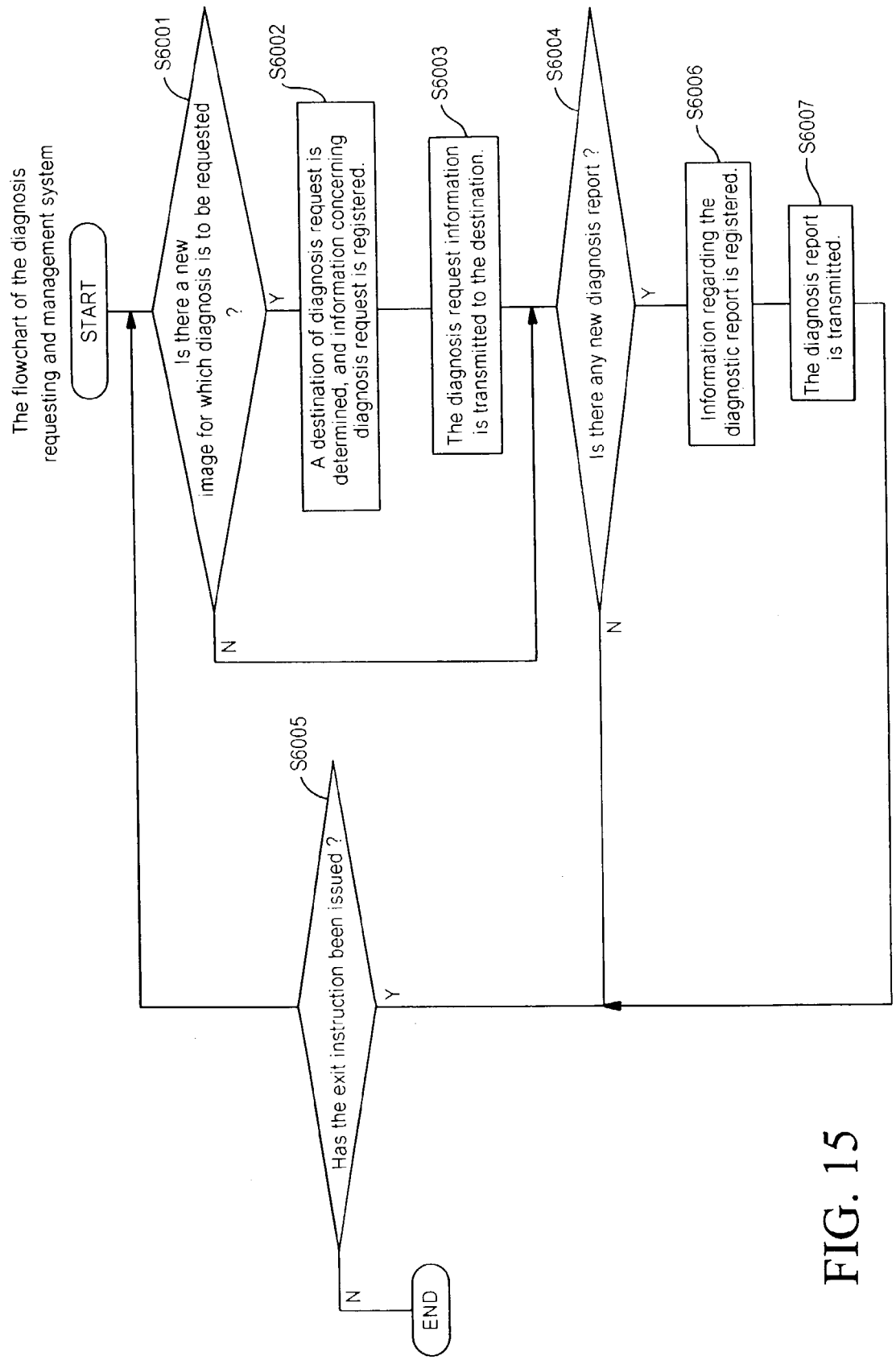
FIG. 15 is a flowchart of a diagnosis requesting and management system according to the present invention.

Next, a procedure of processing by the diagnosis requesting and management system 2009 will be described with reference to a flowchart shown in FIG. 15. First, in step S6001, whether radiographic image data for each patient for which diagnosis is to be requested is present is determined. The determination is made based on information regarding radiographic image data for each patient, transmitted from the imaging system 2003, the medical facility 2000', or the diagnosis intermediating facility 4000, etc., for example, information for accessing image data transmitted to PACS, etc. If the image data is present, the diagnosis requesting and management system 2009 proceeds to step S6002, whereas it proceeds to step S6004 if the image data is not present.

In step S6002, a destination of diagnosis request for images for which diagnosis is to be requested is determined. Furthermore, in order to manage progress of diagnosis, information concerning diagnosis request including information of the destination of diagnosis request is registered in a storage unit. The destination is determined based on information concerning the images, for example, information stored in the storage unit, as header information of the image data, etc., associated with the images (e.g., body part to be imaged of a patient, imaging method diagnostic purpose, disease information, diagnostician designation information, etc.). The destination may be, as described above, the medical facility 2000' or the diagnosis intermediating facility 4000. Then, in step S6003, the diagnosis request information including information for identifying images to be diagnosed or image data to be diagnosed is transmitted to the destination that has been determined.

Then, in step S6004, it is determined whether any new diagnosis report is present. The determination is made based on information received from the diagnosis terminal 2010 or 2011, the medical facility 2000', or the diagnosis intermediating facility 4000, etc. If any new diagnosis report is present, the diagnosis requesting and management system 2009 proceeds to step S6006, whereas it proceeds to step S6005 if no new diagnosis report is present. In step S6005, it is determined whether an exit instruction has been issued to the diagnosis requesting and management system 2009. If an exit instruction has been issued, the diagnosis requesting and management system 2009 exits the procedure. If no exit instruction has been issued, the diagnosis requesting and management system 2009 returns to step S6001 to continue operation.

In step S6006, as part of diagnosis progress management, information regarding a diagnostic report (acquisition date, report content, etc.) is registered in the storage unit. Then, in step S6007, the diagnosis report is transmitted (forwarded) to a predetermined destination such as the HIS 2001, the RIS 2002, the PACS 2006, or the origin of the diagnosis request (such as the medical facility 2000' or the diagnosis intermediating facility 4000, etc.). Then, the diagnosis requesting and management system 2009 proceeds to the determination in step S6005 described earlier.

Although the diagnosis requesting and management system 2009 has been described as implemented by a dedicated computer, without limitation thereto, it may be functionally incorporated into the HIS 2001, the RIS 2002, the imaging management/image processing server 2005 in the imaging system 2003, the PACS server 2007 in the PACS 2006, etc.

Furthermore, in the above-mentioned embodiments, although the radiographic system shown in FIG. 1 is constructed so that radiographed images are transmitted (output) to a destination in a predetermined order regardless of the order of radiographing, without limitation thereto, changing of the order to transmit the images corresponding to the above-mentioned embodiments may be performed at the destination. Namely, for instance, even if the imaging system 2003 transmits the radiographic images to the destination in the order of radiographing and PACS 2006 and/or the diagnosis requesting and management system and so on, which are the said destination, transmit the radiographic images and/or the diagnosis request information to the present destination (the diagnosis terminal 2010 and so on) in the predetermined order, the purpose of the present invention can be achieved. In that case, even though the predetermined order is the order in which RIS 2002 and so on request the imaging system 2003 to radiograph, it can be dealt with, for instance, by transmitting the information of the order of radiographing request with the radiographic image data from the imaging system 2003 to its destination as a part of the header information and so on of the radiographic image data.

According to the present invention, examination can be performed actually in a sequence which is different from a prespecified examination sequence, and the output of images can also be performed in a desired sequence. Consequently, ease of operation of examination can be improved.

Furthermore, according to the present invention, even if the photographic sequence is changed from the prespecified sequence, photographed images can be output in such a prespecified sequence. Consequently, arranging and managing photographed images is easy.

In addition, according to the present invention, since the photographic sequence can be changed at a user's discretion regardless of the photographic sequence of the issued photographic request, the photographic efficiency is improved, and the burden on proper positioning of a patient can be reduced. Further, photographs can be output in a desired sequence at a desired place without performing complex operations, yielding the advantage that the diagnosis efficiency is increased.

Many different embodiments of the present invention may be constructed without departing from the spirit and scope of the present invention. It should be understood that the present invention is not limited to the specific embodiments described in this specification. To the contrary, the present invention is intended to cover various modifications and equivalent arrangements included within the spirit and scope of the invention as hereafter claimed. The scope of the following claims is to be accorded the broadest interpretation so as to encompass all such modifications, equivalent and functions.

What is claimed is:

1. A system for handling examination of an object, comprising:

input means for inputting examination request information of radiographic image data including a plurality of radiographic examination methods for the object and each radiographic examination order of the methods; and display means for displaying a list of the inputted examination order of the examination methods, wherein when an examination is not being performed by the examination methods, the display means displays symbols representing the examination methods, and when an examination has been performed by the examination methods, the display means displays the examined radiographic image data instead of the symbols.

2. A system according to claim 1, further comprising:

changing means for changing the radiographic examination order;

control means for controlling a radiographic examination apparatus so as to set an examination condition corresponding to the radiographic examination method in accordance with the changed order;

radiograph generation means for generating radiograph under the condition set by the control means for controlling the radiographic examination apparatus;

radiographic examination means for converting the radiograph into image data; and output means for outputting the converted radiographic image data in accordance with the changed order.

* * * * *

UNITED STATES PATENT AND TRADEMARK OFFICE
CERTIFICATE OF CORRECTION

| | |
|---|---|
| PATENT NO. | : 6,993,114 B2 |
| APPLICATION NO. | : 10/384637 |
| DATED | : January 31, 2006 |
| INVENTOR(S) | : Toru Takasawa |

It is certified that error appears in the above-identified patent and that said Letters Patent is hereby corrected as shown below:

<u>COLUMN 11</u>:

Line 16, "vertabra " should read --vertebra--.

<u>COLUMN 20</u>:

Line 5, "radiograph" should read --a radiograph--.

Signed and Sealed this

Twenty-eighth Day of November, 2006

JON W. DUDAS
*Director of the United States Patent and Trademark Office*